United States Patent [19]
Wang

[11] Patent Number: 5,515,295
[45] Date of Patent: May 7, 1996

[54] METHODS AND SYSTEMS FOR FLUID IDENTIFICATION AND FLOW RATE DETERMINATION

[75] Inventor: Tak K. Wang, Havertown, Pa.

[73] Assignee: Hewlett-Packard Company, Palo Alto, Calif.

[21] Appl. No.: 361,915

[22] Filed: Dec. 22, 1994

Related U.S. Application Data

[63] Continuation of Ser. No. 611,425, Nov. 9, 1990, abandoned.

[51] Int. Cl.$^6$ .................................................. G01F 1/688
[52] U.S. Cl. ................ 364/510; 364/571.01; 73/861.01; 73/204.11; 73/204.16; 73/204.26
[58] Field of Search ..................................... 364/497, 500, 364/510, 571.01; 73/861, 861.01, 204.11, 204.14, 204.16, 204.27, 204.22, 204.26

[56] References Cited

U.S. PATENT DOCUMENTS

| | | | |
|---|---|---|---|
| 4,070,908 | 1/1978 | Newell | 364/573 X |
| 4,122,722 | 10/1978 | Newell | 364/573 X |
| 4,375,667 | 3/1983 | Buchan | 364/510 X |
| 4,475,388 | 10/1984 | Kawai et al. | |
| 4,485,449 | 11/1984 | Knauss | 364/510 |
| 4,581,714 | 4/1986 | Reid | 364/563 X |
| 4,581,946 | 4/1986 | Kanayama | 364/510 X |
| 4,638,443 | 1/1987 | Kaneyasu et al. | 364/497 |
| 4,812,747 | 3/1989 | Gale et al. | 364/573 X |
| 4,847,783 | 7/1989 | Grace et al. | 364/497 |
| 4,884,215 | 11/1989 | Zboralski et al. | 364/510 |
| 4,944,035 | 7/1990 | Aagardyl | 364/556 |
| 5,177,696 | 1/1993 | Bonne | 364/556 X |

FOREIGN PATENT DOCUMENTS

| | | |
|---|---|---|
| 0373965 | 6/1990 | European Pat. Off. . |
| 0387025 | 9/1990 | European Pat. Off. . |
| 0395126 | 10/1990 | European Pat. Off. . |
| 2374639 | 12/1977 | France . |
| 91/19170 | 12/1991 | WIPO . |

OTHER PUBLICATIONS

Omega "Flow Measurement & Control Handbook & Encyclopedia", 1985; pp. D5–D9 & J7–J8.
Johnson, R. G., and Higashi, R. E., *Sensors and Actuators*, 1987, 11, 63–72.
Senors & Actuators, vol. 11, No. 1, 1st Jan. 1987, pp. 63–72, Lausanne, CH, R. G. Johnson et al: "A highly sensitive silicon chip microtransducer for air flow and differential pressure sensing applications".

Primary Examiner—Emanuel T. Voeltz
Assistant Examiner—Kyle J. Choi
Attorney, Agent, or Firm—Mark Z. Dudley

[57] ABSTRACT

Methods and systems for determining the identity and flow rate of a fluid are provided. Linearized output signals are provided. To determine fluid flow, a test fluid is passed through a conduit. A heater associated with the conduit is maintained a temperature greater than the temperature of the conduit in the presence of the test fluid. A measuring voltage is generated, wherein the measuring voltage is indicative of the voltage required to maintain the heater at the specified temperature. A data set is provided to a computer, which compares the measuring voltage with a reference voltage and determines the identity of the test fluid. Further, a flow function is applied to the data set and the fluid flow rate is calculated.

16 Claims, 8 Drawing Sheets

METHODS AND SYSTEMS FOR FLUID IDENTIFICATION AND FLOW RATE DETERMINATION

CROSS REFERENCE TO RELATED APPLICATION(S)

This is a continuation of application Ser. No. 07/611,425 filed on Nov. 9, 1990, now abandoned.

BACKGROUND OF THE INVENTION

This invention relates to methods and systems for identifying fluids and determining fluid flow rates and, more particularly, to methods and systems for determining gas flow rates using a hot wire anemometer.

Instruments which rely upon controlled fluid flow are commonly employed in a wide variety of applications, such as sample purification, chemical analysis, clinical assay, and industrial processing. Many instruments, such as high pressure liquid chromatographs (HPLC), gas chromatographs (GC), clinical analyzers, and flow-injection analyzers, require precisely-controlled flow.

It is known in the art to determine gas flow rates by determining the flow rate with a hot wire anemometer. In a hot wire anemometer, the gas typically is passed over a single heated wire, reducing the temperature of the wire. The change in resistance of the heated wire is determined and correlated with the flow rate of the gas. A more advanced technique employs two temperature sensing elements located a fixed and equal distance from a heat source. The gas is passed through the system, reducing the temperature of the upstream sensor and increasing the temperature of the downstream sensor. The temperature difference is then recorded as an output signal.

One major drawback of hot wire anemometers is the nonlinear and fluid-dependent manner in which they respond to fluid flow. Thus, the output signal is rarely useful by itself and must typically be augmented by other data. For applications wherein multiple gases are employed, both gas type information and the calibration curves corresponding to each of the different gases are necessary to determine the flow rate. A computer can be used to linearize or calculate flow rate from calibration curves. However, gas type information must first be fed into the computer in order to do so. Data processing in this manner requires initial identification of the gas and the performance of time-consuming data input steps.

It would thus be of great advantage in determining fluid flow to provide a flow system which is capable of automatically identifying the type of fluid passing through the system. It would also be of great advantage to provide a system which is capable of determining the flow rates of different fluids from a single, linearized response curve.

SUMMARY OF THE INVENTION

The present invention provides methods and systems for determining the identity of a fluid, methods and systems for determining the fluid's flow rate, and methods and systems for linearizing output signals provided by flow determination systems.

The methods for determining fluid identity are preferably performed using a conduit which comprises heating means and a voltage source coupled with the heating means, capable of providing input voltage thereto. Preferred identification methods comprise passing a test fluid through the conduit, maintaining the heating means at a temperature greater than the temperature of the conduit in the presence of the test fluid, generating a test input voltage required to maintain the heating means at said temperature, providing to a processing means a data set comprising the test input voltage, and comparing the test input voltage with at least one reference input voltage to determine the identity of the test fluid.

The methods for determining the fluid flow rate are preferably performed using systems which comprise a conduit, output means, and a voltage source. The conduit preferably comprises a first sensor, a second sensor a first predetermined distance from the first sensor, and heating means a second predetermined distance from both the first sensor and the second sensor. The output means is preferably coupled with the first sensor and the second sensor and is capable of generating an output signal representative of the difference in temperature therebetween. The voltage source is preferably coupled with the heating means and is capable of providing input voltage thereto.

Preferred methods for determining fluid flow comprise determining the identity of the fluid, passing the fluid through the conduit, maintaining the heating means at a temperature greater than the temperature of the conduit, generating an output signal, and providing to processing means a data set which comprises the output signal. The methods further comprises applying, via the processing means, a flow function to the data set. In one preferred method, the flow function is applied to the data set according to:

$$u = (\rho C_p L/k)^{-1} * [Log_e(\Psi) - Log_e(\Psi - \Delta T)]$$

where u is the flow rate, $\rho$ is the density of the fluid, $C_p$ is the thermal capacity of the fluid, L is the second predetermined distance, k is the thermal conductivity of the fluid, $\Psi$ is constant which depends upon the geometry of the conduit, and $\Delta T$ is the temperature difference between the first sensor and the second sensor.

The methods for linearizing output signals are preferably performed with the flow determination systems of the invention and comprise passing a test fluid through the conduit at a plurality of flow rates, maintaining the heating means at a temperature greater than the temperature of the conduit, generating a plurality of test output signals at each of the plurality of flow rates, providing to a processing means a data set which comprises the plurality of test output signals; and applying, via the processing means, a linearizing function to the data set. Preferably, the linearizing function is applied to the data set according to:

$$f = +\beta_{test} * [Log_e(\alpha_{test}) - Log_e(\alpha_{test} - v_o)]$$

where f is the linearized output signal, $\alpha_{test}$ and $\beta_{test}$ are experimentally derived constants dependent upon the conduit and the test fluid, and $v_o$ is the test output signal.

DETAILED DESCRIPTION OF THE INVENTION

The methods and systems of the present invention may be employed to identify and determine the flow rates of a wide variety of fluids. Fluids include gases, liquids, supercritical fluids, plastic solids, multiple component gases and liquids, and mixtures of solids and liquids capable of flow. Gases are preferred fluids according to the present invention.

The fluid identification methods may be practiced in a wide variety of systems which comprise a conduit. It will be appreciated that the term conduit encompasses any tube, pipe, or other vessel having the capacity to substantially contain and direct the flow of the fluid passed therethrough. Preferred conduits are fabricated from a wide variety of materials having at least minimal thermal conductivity. Conduits according to the present invention comprise a heating means substantially contained within the conduit. The heating means may be any of those known in the art. Preferred heating means comprise electrically resistive materials.

A voltage source is preferably coupled with the heating means. Any of the wide variety of voltage sources known in the art are suitable for employment in the present invention, so long as they are capable of providing an input voltage to the heating means in order to maintain the heating means at a predetermined temperature. It is preferred that the predetermined temperature be greater than the temperature of the conduit, more preferably greater than the inside wall of the conduit. Preferred voltage sources are capable of providing a variable voltage to the heating means to maintain the predetermined temperature.

Preferred fluid identification systems further comprise processing means coupled with both the voltage source and the output means. Processing means amenable to the practice of this invention consist of a computing device such a microprocessor, microcontroller, capacitor, switch, logic gate, or any equivalent logic device capable of compiling and executing instructions. Processing means preferably are coupled with a data input means such as a keyboard and a data output means such as a video display or printer. Preferred processing means further include one or more devices for the storage of data, such as magnetic disks or tape. Processing means preferably also comprise an operating system or programming environment for the generating of source code in the appropriate programming language, along with a compiler or other means of converting such source code into executable programs.

Figure 1:
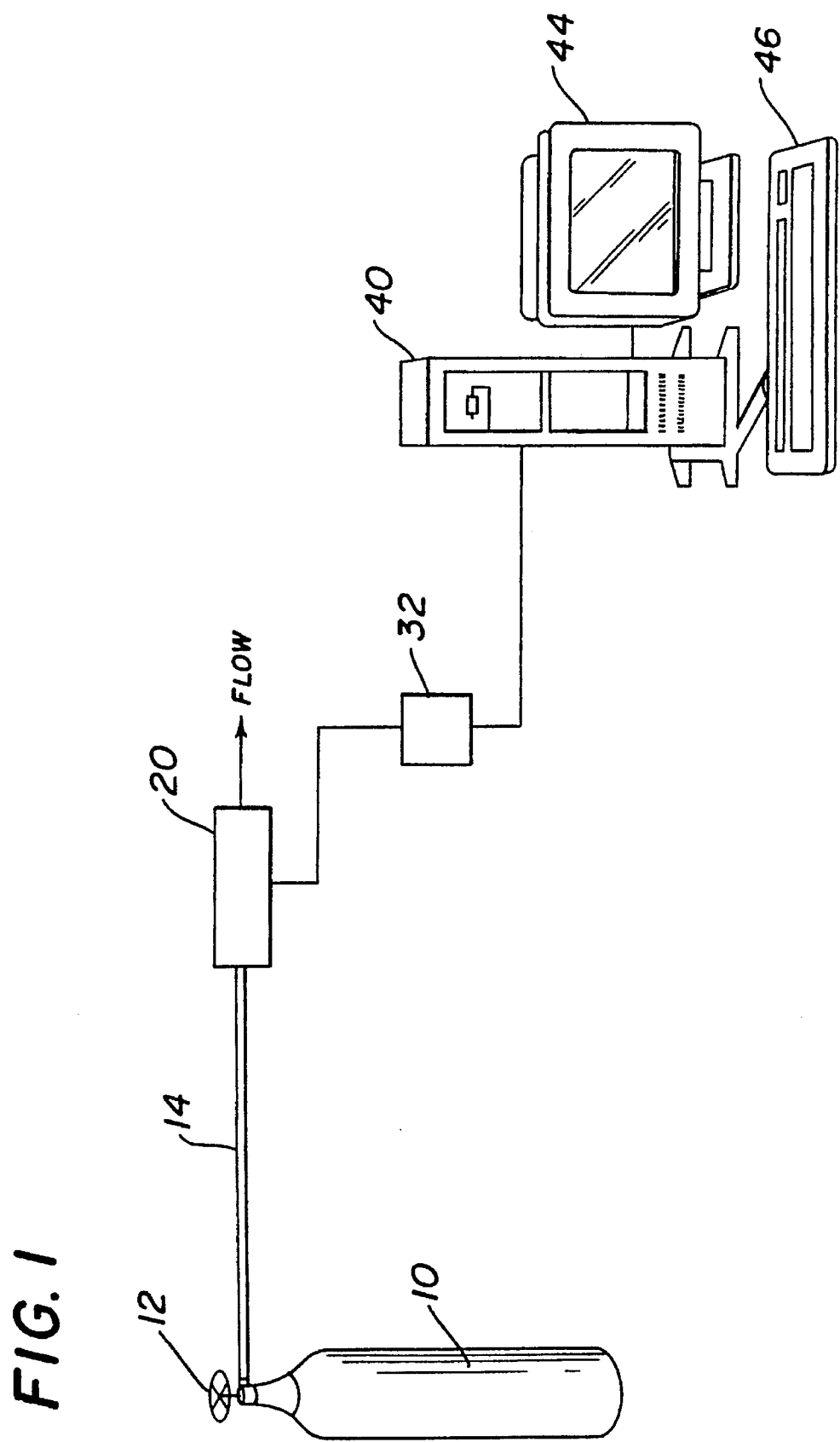
FIG. 1 depicts a fluid identification system according to the present invention.
Figure 2A:
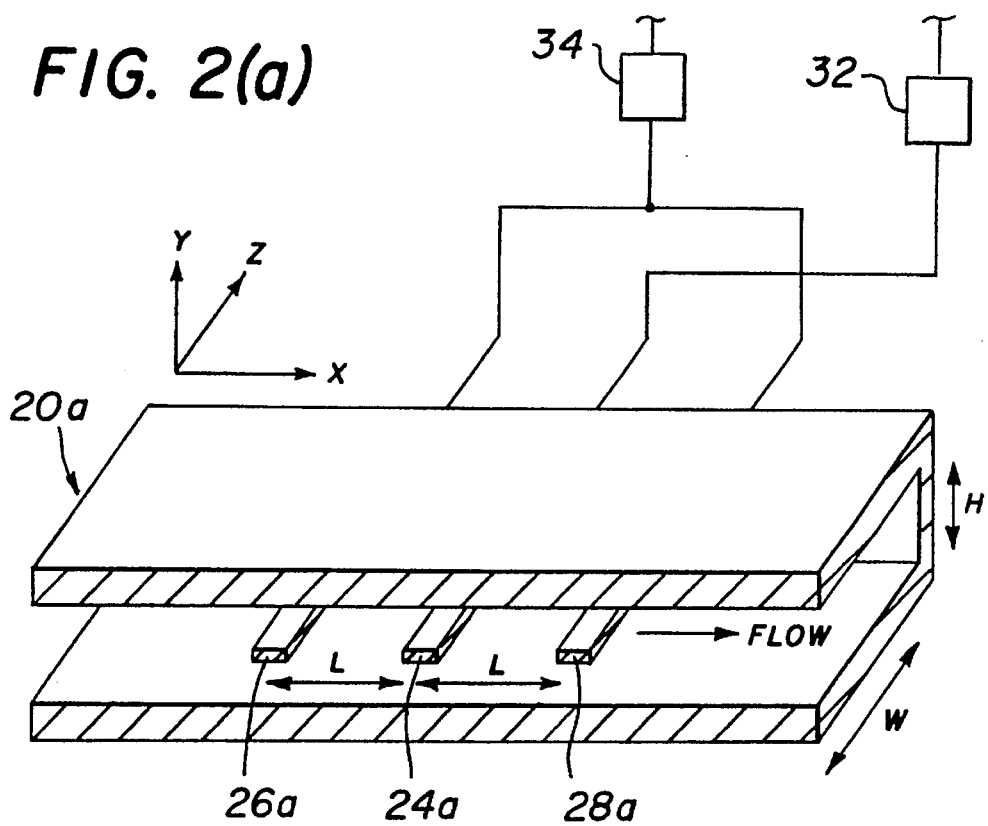
FIG. 2a is a perspective view of a conduit according to the present invention, wherein the front portion thereof has been omitted.
Figure 2B:
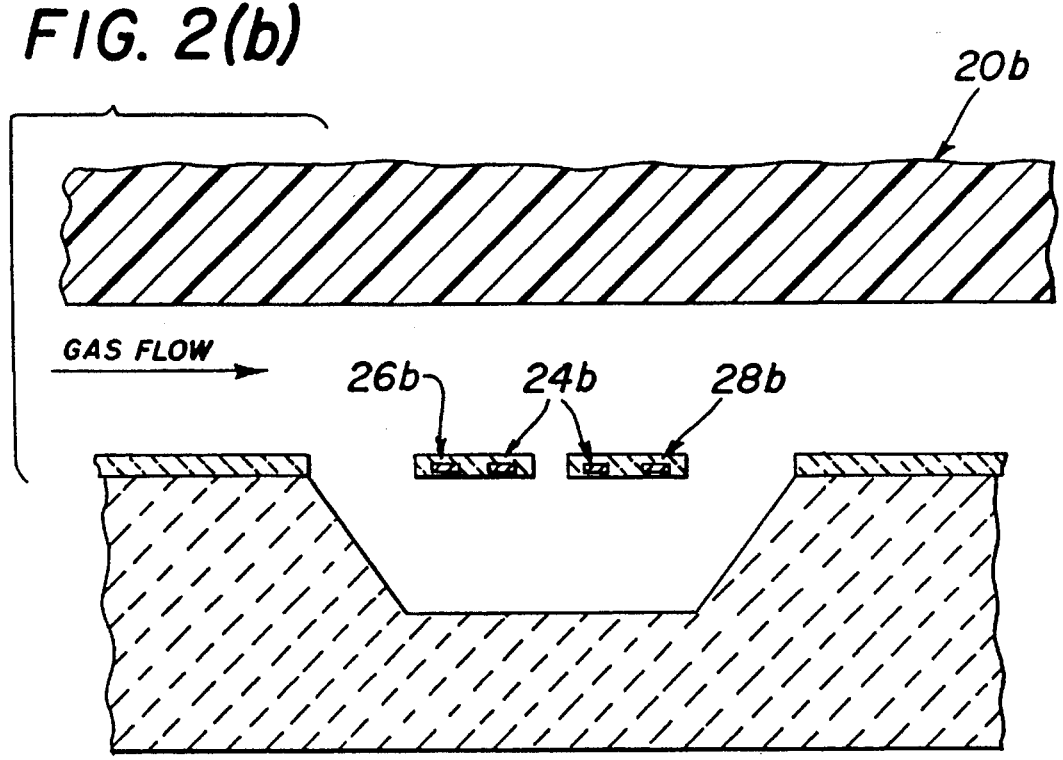
FIG. 2b is a cross-sectional view of a conduit according to the present invention.

One preferred fluid identification system is depicted in FIG. 1. This system comprises a fluid source (10) having metering means (12) for increasing or decreasing the flow rate of the fluid. The metering means may be any of those known in the art, such as valves, nozzles, and needles. A preferred fluid source is a canister which comprises pressurized gas. The fluid source is placed in fluid communication with a conduit (20) by way of tubing, piping, or some other suitable means (14) for transporting the fluid to the conduit. Preferred conduits according the present invention are depicted in FIGS. 2a and 2b. The conduit of FIG. 2b is commercially-available from the MicroSwitch Company of Freeport, Ill. Conduits useful for fluid identification comprise a heating means (24a or 24b). Preferred fluid identification systems further comprise a voltage source (32) coupled with the heating means and with a processing means (40) which is, in turn, coupled with a data output means (44) and a data input means (46).

Methods for determining the identity of test fluids in systems such as described above comprise passing the test fluid through the conduit. This is typically accomplished by opening a valve on a gas cylinder connected with the conduit. A test input voltage is then applied to the heating means in order to maintain the heating means at a temperature greater than the temperature of the conduit in the presence of the test fluid.

A data set comprising the test input voltage is next provided to the processing means. Preferably, the processing means comprises at least one reference input voltage. A reference input voltage is the input voltage required to maintain the heating means at a temperature greater than the temperature of the conduit in the presence of a reference fluid at a zero flow rate. Reference input voltages are preferably compiled by passing the reference fluid through the conduit, terminating passage of the reference fluid, applying a reference input voltage to the heating means, and recording the reference input voltage.

The test input voltage is then compared with at least one reference input voltage via the processing means to determine the identity of the test fluid. The input voltage required to maintain the temperature of the heating means in the presence of the fluid is believed to be a unique characteristic of the fluid. Thus, when the reference input voltages provided to the processing means correspond to hydrogen, nitrogen, and oxygen gas and the test input voltage is identical to the reference input voltage for hydrogen gas, it can reasonably be concluded that the reference fluid comprises hydrogen gas.

However, the input voltage for a fluid is to some degree dependent upon the fluid's flow rate. Thus, an unknown gas may be identified with greater accuracy where its flow rate is known or at least approximated. A list of input voltages for different known gasses at different output signals can be stored in the processing means. The input voltage and flow rate for an unknown gas can then be compared to the list to determine the identity of the unknown gas.

The present invention also provides methods for determining the flow rate of a fluid. These methods may be practiced in a wide variety of systems. Preferably, the systems comprise means for identifying the fluid. Preferred flow determination systems further comprise a conduit and metering means for passing the fluid through the conduit at a fixed rate. The conduit comprises a first sensor and a second sensor a first predetermined distance from the first sensor. The sensors preferably are selected from any of the temperature sensors known in the art. Preferred temperature sensors are temperature dependent resistors, diodes or transistors. The conduit further comprises a heating means located a second predetermined distance from both the first sensor and the second sensor.

The flow determination systems further comprise output means coupled with the first sensor and the second sensor and capable of generating an output signal representative of the temperature difference between the first sensor and the second sensor. The flow determination systems preferably further comprises a voltage source coupled with the heating means, capable of providing input voltage thereto.

Figure 3:
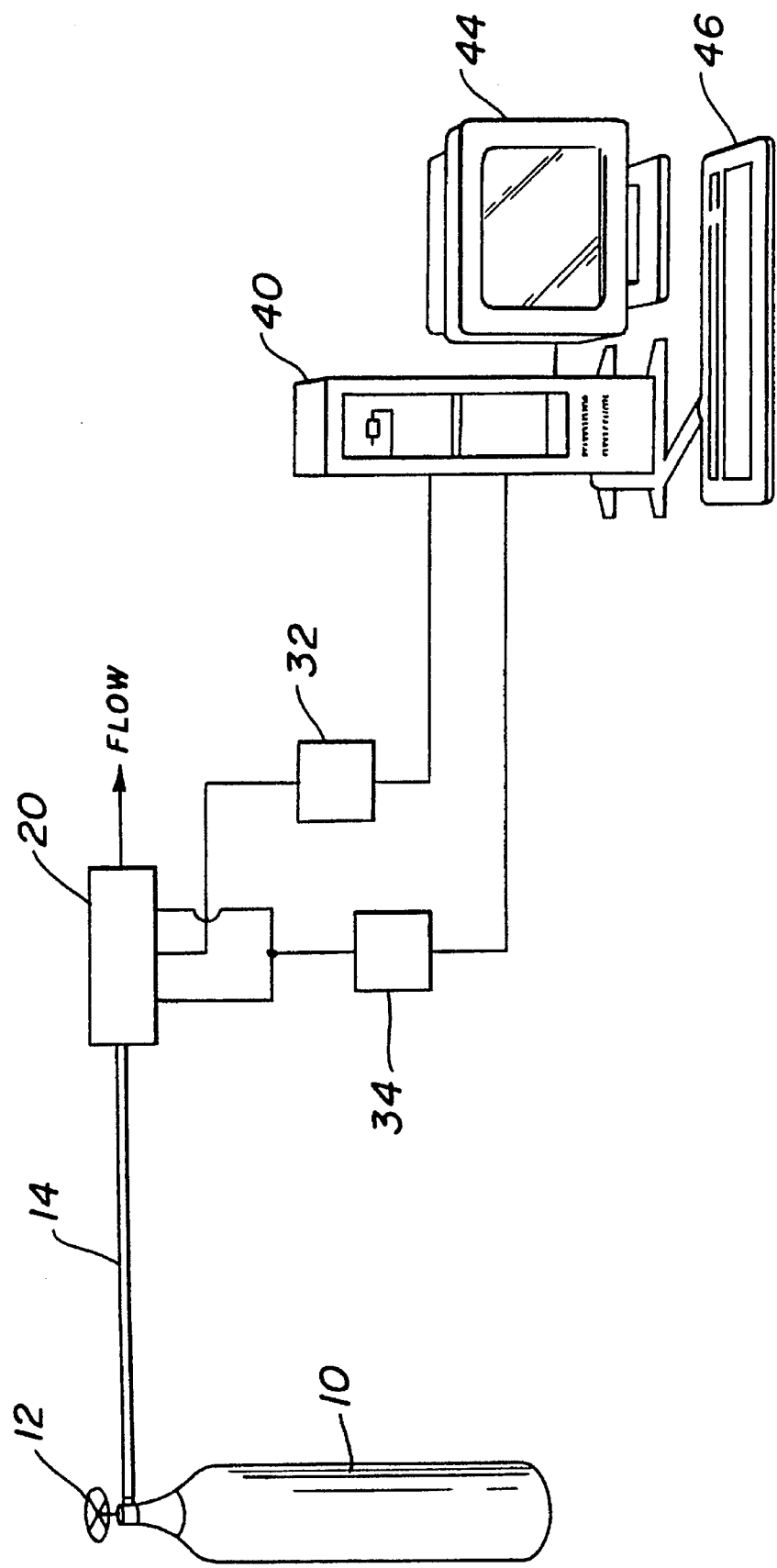
FIG. 3 depicts a flow determination system according to the present invention.

A preferred flow determination system is depicted in FIG. 3. This system comprises a fluid source (10) having metering means (12) for increasing or decreasing the flow rate of the fluid. A preferred fluid source is a canister which comprises pressurized gas. The fluid source is placed in fluid communication with a conduit (20) by way of tubing, piping, or some other suitable means (14) for transporting the fluid to the conduit. Preferred conduits for fluid determination are depicted in FIGS. 2a and 2b and comprise a heating means (24a or 24b), a first sensor (26a or 26b), and a second sensor (28a or 28b).

Figure 4:
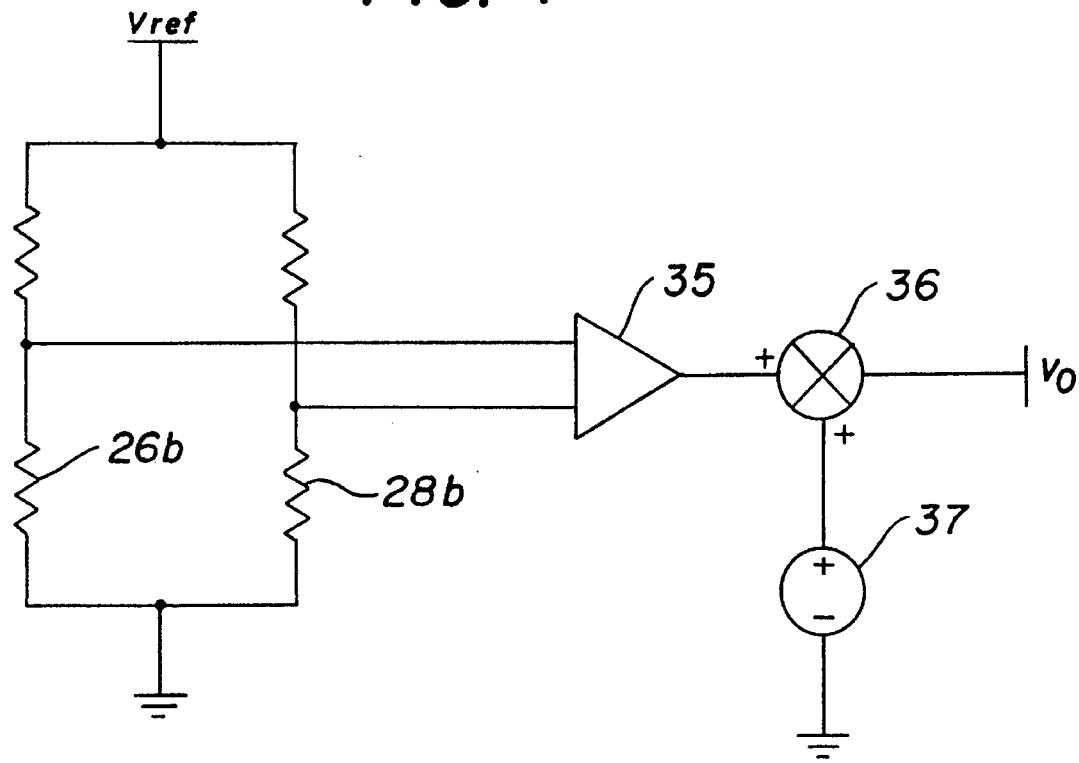
FIG. 4 depicts a circuit useful in a flow determination system according to the present invention.

The fluid determination systems further comprise an output means (34) coupled with the first sensor and the second sensor. A preferred output means is depicted in FIG. 4, wherein the first sensor (26b) and the second sensor (28b) are arranged together with resistor elements in a Wheatstone bridge configuration to produce an output signal ($v_o$) via a differential amplifier (35). Preferred output means further comprise means for signal addition (36) and means for providing offset voltage (37). The first sensor and the second sensor may alternatively be coupled with two constant current sources such that a change in the sensor resistance due to a change in temperature will effect a change in the output signal and the output means amplifies the voltage output.

The fluid determination system depicted in FIG. 3 further comprises a voltage source (32) coupled with the heating means and with a processing means (40). The processing means is preferably coupled with a data output means (44) and a data input means (46).

The preferred methods for determining the flow rate of a fluid in the described systems comprise determining the identity of the fluid. The identity of the fluid may be determined by the methods of the present invention or by some alternative means. Preferred fluid determination methods further comprise passing the test fluid through the conduit at a fixed flow rate, maintaining the heating means at a temperature greater than the temperature of the conduit in the presence of the test fluid, and generating an output signal representative of the difference in temperature between the first sensor and the second sensor. A data set which comprises the output signal is then provided to the processing means and a flow function is applied to the data set via the processing means to calculate the flow rate.

Where it is desired to control fluid flow by maintaining a predetermined flow rate, the calculated (actual) flow rate may then be compared with the predetermined flow rate. If the calculated flow rate is greater than the predetermined flow rate, the flow rate is decreased by, for example, incrementally closing the valve on the tank. If the calculated flow rate is less than the predetermined flow rate, the flow rate is increased by incrementally opening the valve on the tank.

A number of flow functions are employable in the present invention and are derived by analyzing a conduit such as depicted in FIG. 2a. Those skilled in the art will appreciate that the simplified form of the energy equation for gas flow for a conduit such as depicted in FIG. 2a can be expressed as:

$$\frac{\partial^2 T}{\partial x^2} + \frac{\partial^2 T}{\partial y^2} = \frac{\rho C_p u}{k} \frac{\partial T}{\partial x} \tag{1}$$

where $\rho$, $k$, $C_p$ and $u$ are the density, thermal conductivity, thermal capacity and the x-direction flow velocity of the gas. If viscosity, pressure variation, and flow velocity in the y and z directions are neglected, re-arranging Equation 1 provides:

$$\frac{\partial^2 T}{\partial x^2} - \frac{\rho C_p u}{k} \frac{\partial T}{\partial x} = \frac{\partial^2 T}{\partial y^2} \tag{2}$$

Substituting the identity $T(x,y)=G(x) F(y)$ into Equation 2 yields Equations 3 and 4.

$$\frac{1}{F} \cdot \frac{\partial^2 F}{\partial y^2} = -\lambda^2 \tag{3}$$

$$\frac{1}{G}\left[\frac{\partial^2 G}{\partial x^2} - \frac{\rho C_p u}{k} \frac{\partial G}{\partial x}\right] = -\lambda^2 \tag{4}$$

The solution of Equation 3 is given by the sum of the eigenfunctions:

$$F(y) = \sum_{n=-\infty}^{+\infty} A_n \cos(\lambda_n y) + B_n \sin(\lambda_n y) \tag{5}$$

where $\lambda_n$ are eigenvalues given by $2(n+1)\pi/4H$ and $A_n$ and $B_n$ are coefficients to be determined by the boundary conditions. Equation 4 can be solved in terms of $\lambda_n$. The characteristic roots of Equation 4 for each $\lambda_n$ are:

$$m_{1,2} = (\rho C_p u/2k) \pm [(\rho C_p u/2k)^2 + \lambda_n^2]^{0.5} \tag{6}$$

Thus, $G(x)$ can be expanded according to Equation 7.

$$G(x) = C_n EXP\{(\rho C_p u/2k) + [(\rho C_p u/2k)^2 + \lambda_n^2]^{0.5}\}x + D_n EXP\{(\rho C_p u/2k) - [(\rho C_p u/2k)^2 + \lambda_n^2]^{0.5}\}x \tag{7}$$

For $x>0$, the second exponential function tends to infinity and is not admissible; that is, $D_n=0$. Similarly, $C_n=0$ for the solution with $x<0$. Thus, we have Equations 8 and 9.

$$G(x>0) = C_n EXP\{(\rho C_p u/2k) + [(\rho C_p u/2k)^2 + \lambda_n^2]^{0.5}\}x \tag{8}$$

$$G(x<0) = D_n EXP\{(\rho C_p u/2k) - [(\rho C_p u/2k)^2 + \lambda_n^2]^{0.5}\}x \tag{9}$$

These two equations are equal at $x=0$. Thus, $C_n=D_n$. By combining $F(y)$ and $G(x)$ and taking temperature differences at $x=L$ and $x=-L$, one obtains Equation (10).

$$\Delta T = \sum_{n=-\infty}^{+\infty} C_n [A_n \cos(\lambda_n y) + B_n \sin(\lambda_n y)] * \tag{10}$$

$$SINH(\rho C_p u L/2k) * EXP\{-[(\rho C_p u L/2k)^2 + (\lambda_n L)^2]^{0.5}\}$$

Thus, the temperature difference between two points equally spaced from the heating means is a function of the flow velocity, $u$, and the thermal diffusivity. Further simplification to Equation 11 is possible by assuming $\lambda_n << \rho C_p u/2k$.

$$\Delta T = \Psi (1 - EXP[-\rho C_p u L/k]) \tag{11}$$

where $$\Psi = \sum_{n=\infty}^{+\infty} C_n [A_n \cos(\lambda_n y) + B_n \sin(\lambda_n y)] \tag{12}$$

The term $\Psi$, which is expressed as a temperature, depends upon the geometry of the conduit employed and the position therein of the sensors and the heating means. Those skilled in the art will recognize that the calculation of $\Psi$ can be quite rigorous. An experimentally-derived substitute for $\Psi$ can be more easily determined by, for example, passing a known gas through the conduit at a plurality of known flow rates. The temperature difference ($\Delta T$) between the sensors is then determined at each flow rate and transformed into an output signal ($v_o$) by way of an appropriate circuit. The output signals are then compared with the known flow rates. Typically, the output signals will differ from their corresponding known flow rate by the same voltage amount, $G_s$. Like $\Psi$, $G_s$ is dependent upon the conduit. Hence, $G_s$ and $\Psi$ may in certain applications be substituted for one another in applying flow functions according to the present invention, as may $\Delta T$ and $v_o$.

Equation 11 can be inverted to obtain flow velocity as a function of the temperature difference between the first sensor and the second sensor, as shown in Equation 13.

$$u=(\rho C_p L/k)^{-1}*[Log_e(\Psi)-Log_e(\Psi-\Delta T)]( \tag{13}$$

By assuming u proportional to volumetric or mass flow, a relation is derived between the flow rate and the temperature difference between the sensing elements. Hence, the volumetric or mass flow rate can be determined by determining the temperature difference between the first sensor and the second sensor.

The present invention will now be further described by reference to the following examples thereof, which are not intended to be limiting.

EXAMPLE 1

A system similar to that depicted in FIGS. 3, 2b, and 4 was established, except that a Model 821 Top=Trak™ flow monitor by the Sierra Instrument Co. of Carmel Valley, Calif. was placed between a gas canister (10) and the conduit (20) to accurately determine the fluid flow rate. The first sensor 26(b) and the second sensor 28(b) were temperature dependent resistors. The processing means (40) was a Hewlett-Packard Vectra™ computer.

Air, hydrogen gas, and helium gas contained in canisters were individually passed through the conduit. Various volumetric flow rates were effected by adjusting the valve (12) on the canister. These rates were determined with the flow monitor and recorded. An input voltage sufficient to maintain the heating means at 160° C. above the temperature of the conduit was provided. These reference input voltage were recorded, along with the output signals corresponding to the various flow rates.

Figure 5:
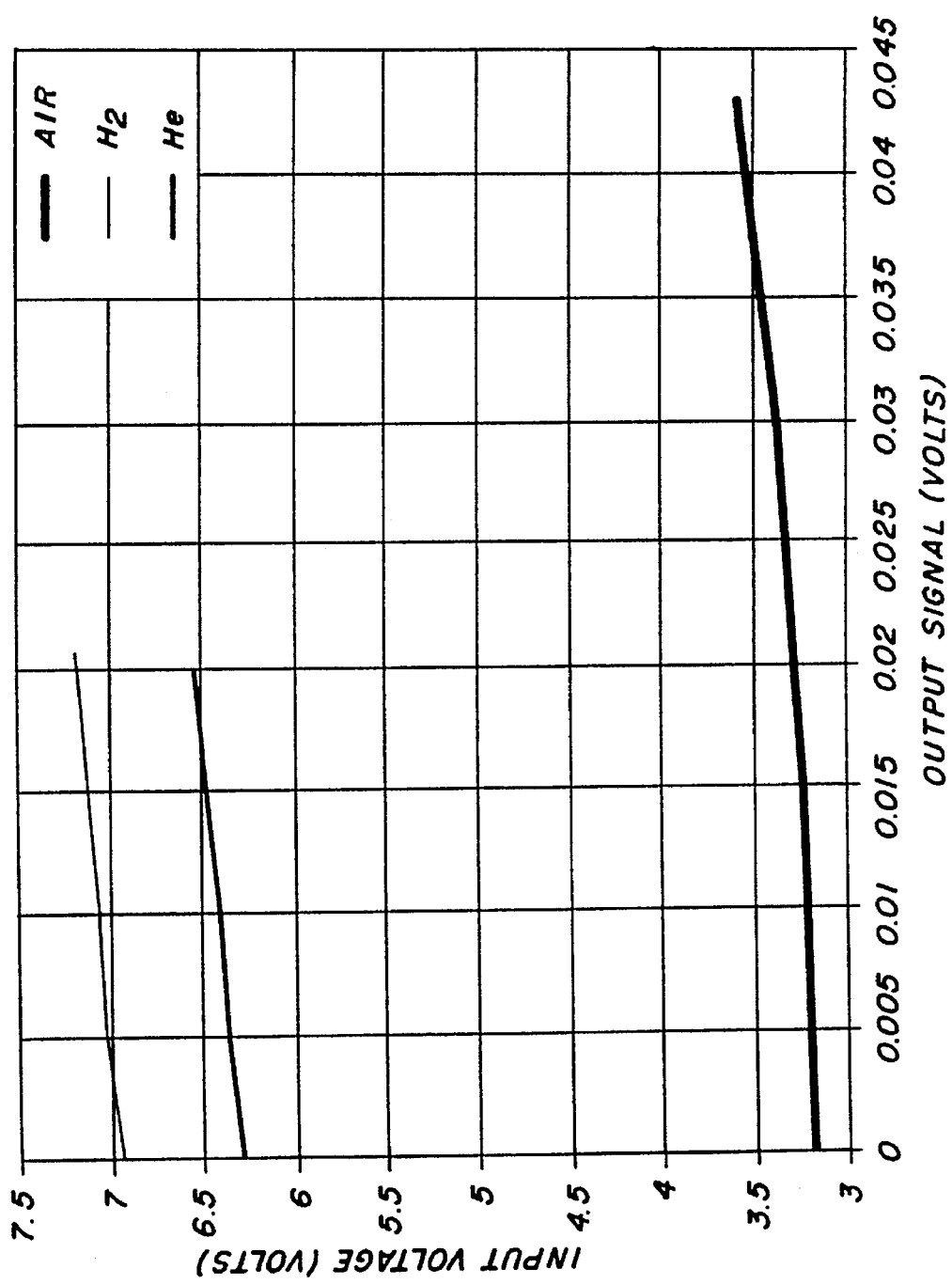
FIG. 5 is a graphical representation of output signal versus input voltage for three gases.

FIG. 5 shows the input voltage required at varying signal output levels. As can be seen, input voltage is a strong function of gas type and depends only weakly upon the gas flow rate.

Figure 6:
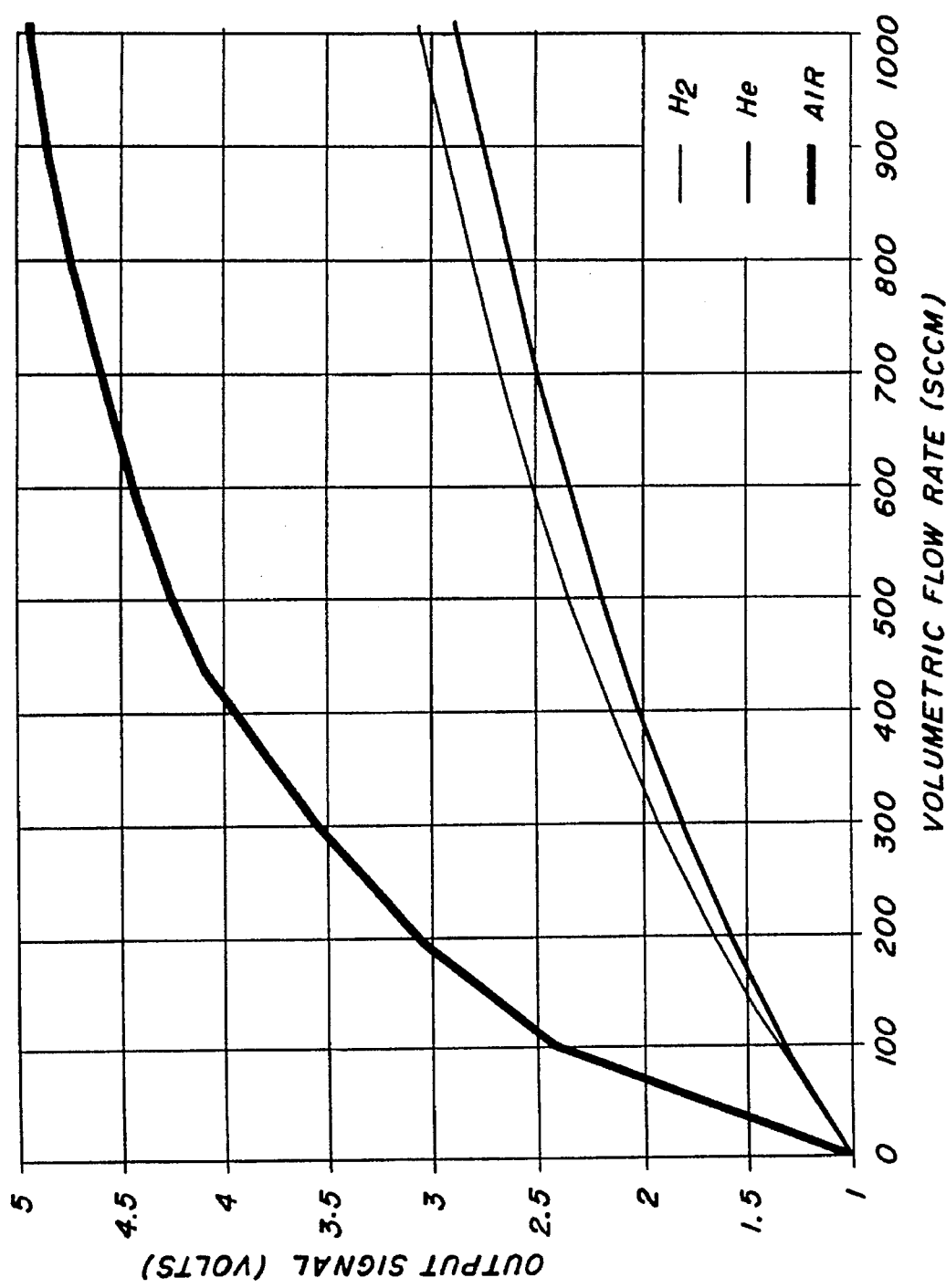
FIG. 6 is a graphical representation of volumetric flow rate versus output signal for three gases.

FIG. 6 shows the output signal versus the volumetric flow rate. The same set of data were plotted in FIG. 7 with the volume flow rate normalized by comparison with a reference fluid, in this case air, according to Equation 14, wherein all gas properties are taken at 20° C. Any gas could have been selected as the reference fluid; similarly, any liquid is believed to be employable as a reference fluid where the test fluid is a liquid.

$$\gamma=\frac{(\rho C_p/k)_{test}}{(\rho C_p/k)_{ref}} \tag{14}$$

Figure 7:
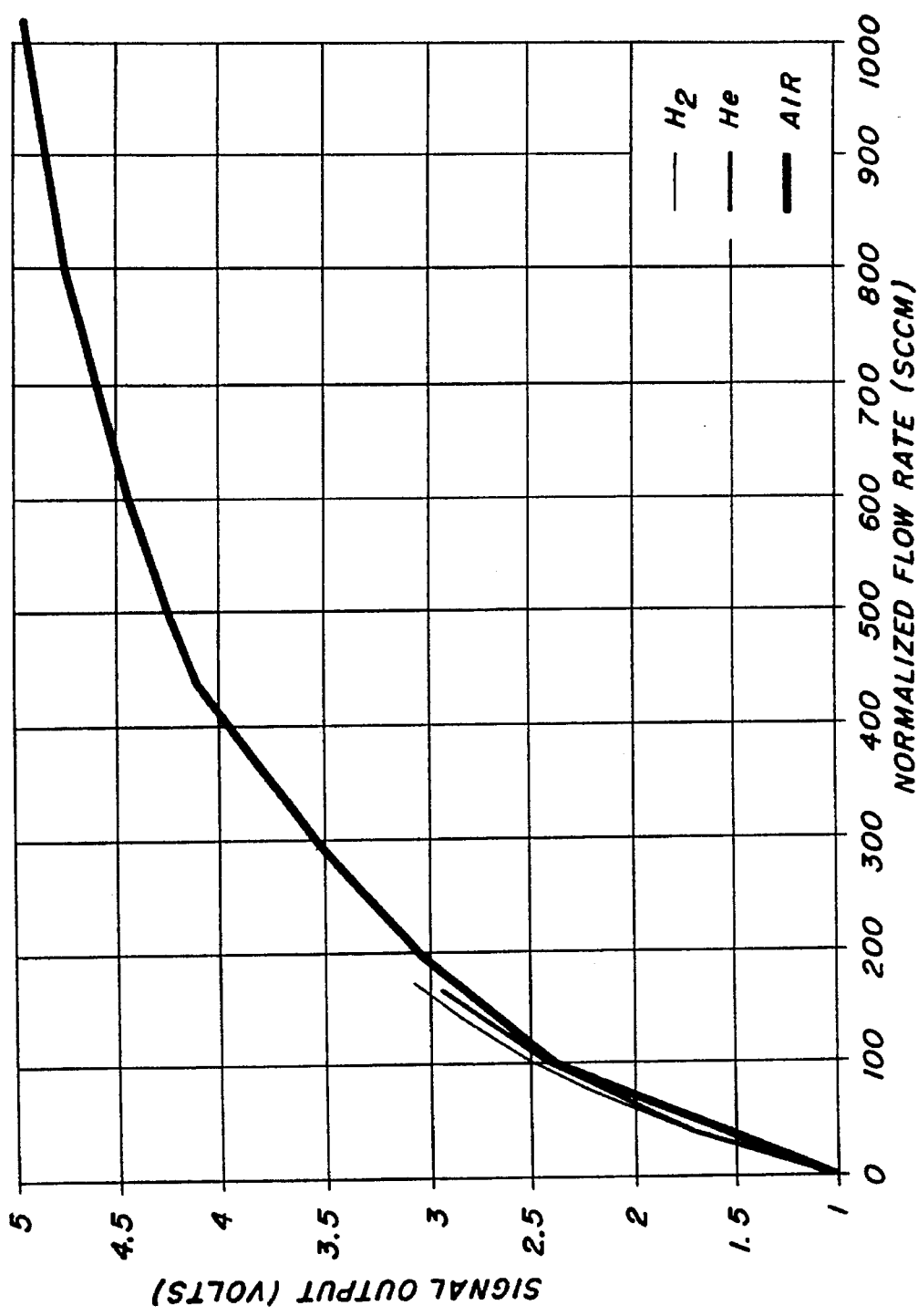
FIG. 7 is a graphical representation of normalized volume flow rate versus output signal for three gases.

It will be recognized that the small discrepancies between the response curves in FIG. 7 can be eliminated by multiplying the normalized flow rate with an experimentally determined factor which was found to range between 0.8 to 1.1 for hydrogen, helium, carbon dioxide and argon.

The experimental data were also fitted, via the processing means, with an equation of the form:

$$f=\beta*[Log_e(\alpha)-Log_e(\alpha-\{v_o-V_{offset}\})] \tag{15}$$

where f is the volumetric flow rate, $\alpha$ and $\beta$ are constants determined by a minimum mean square error fit to the experimental curves, $v_o$ is the output signal and $V_{offset}$ is the output signal at zero flow, 1.0 volts in the present case. Those skilled in the art will recognize that $\alpha$ is related to the properties of the gas and the conduit geometry, whereas $\beta$ is related to the properties of the gas and the cross-sectional area of the conduit. Those skilled in the art will also recognize that mathematical programs are commercially-available for performing minimum mean square error fit to data such as the response curve for a gas. A preferred program is Mathematica™ from Wolfram Research Inc. of Champaign, Ill.

Figure 8:
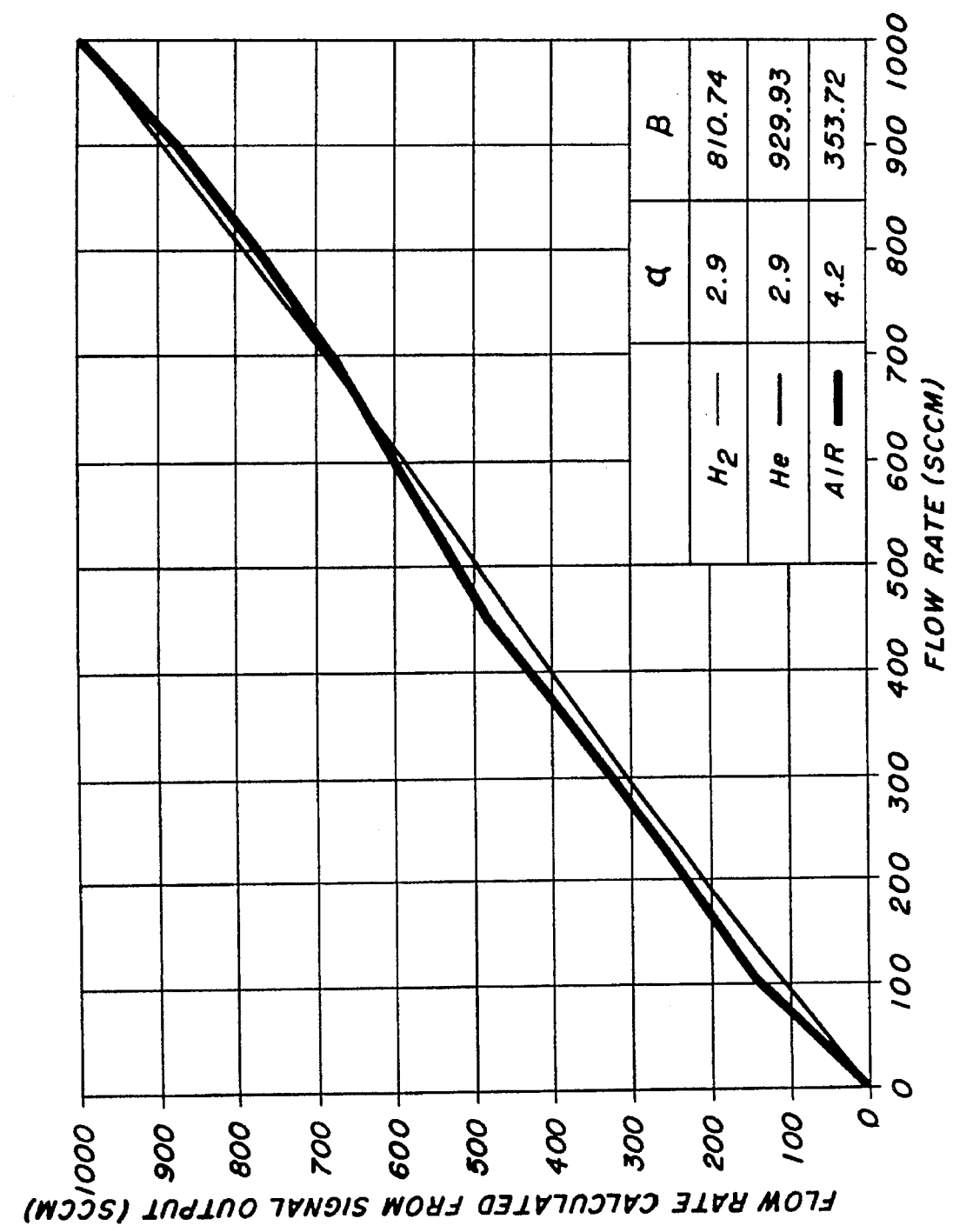
FIG. 8 is a graphical representation of flow rate versus flow calculated from output signal for three gases.

In FIG. 8, f is plotted in a near-linear fashion versus the known volumetric flow rate for the different gases. Thus, application of Equation 15 provides a method for linearizing the output signals for the tested gases. The values for $\alpha$ and $\beta$ for each gas are provided in the legend of the graph in FIG. 8. It will be appreciated that such values such as these which are both experimentally derived and compiled provide one example of reference constants according to the present invention. Reference input voltages and reference output signals are likewise reference constants.

EXAMPLE 2

An unknown test gas is passed at a fixed, yet unknown, flow rate through the system depicted in FIG. 3. It is desired to pass the test gas through the system at a flow rate of 500 sccm. The input voltage required to maintain the heating means 160° C. above the ambient temperature is recorded as 6.3 volts. The output signal is also recorded.

The input voltage and the output signal are provided as a data set to a processing means. The input voltage is compared with the reference input voltages generated in Example 1 and the identity of the test gas is determined to be helium.

Flow function is then applied via the processing means to the data set according to:

$$f=\beta_{test}*[Log_e(G_s)-Log_e(G_s-v_o)] \tag{16}$$

where f is the fixed flow rate, $\beta_{test}$ is the constant determined in Example 1 for helium, $G_s$ is an experimentally derived constant voltage dependent upon the conduit, and $v_o$ is the output signal.

The flow function is solved for f, the flow rate, and found to be 400 sccm. Since this value is lower than 500 sccm, the fixed flow rate is increased. The flow rate is re-calculated and the fixed flow rate adjusted until the calculated flow rate is equal to 500 sccm.

EXAMPLE 3

Figure 9:
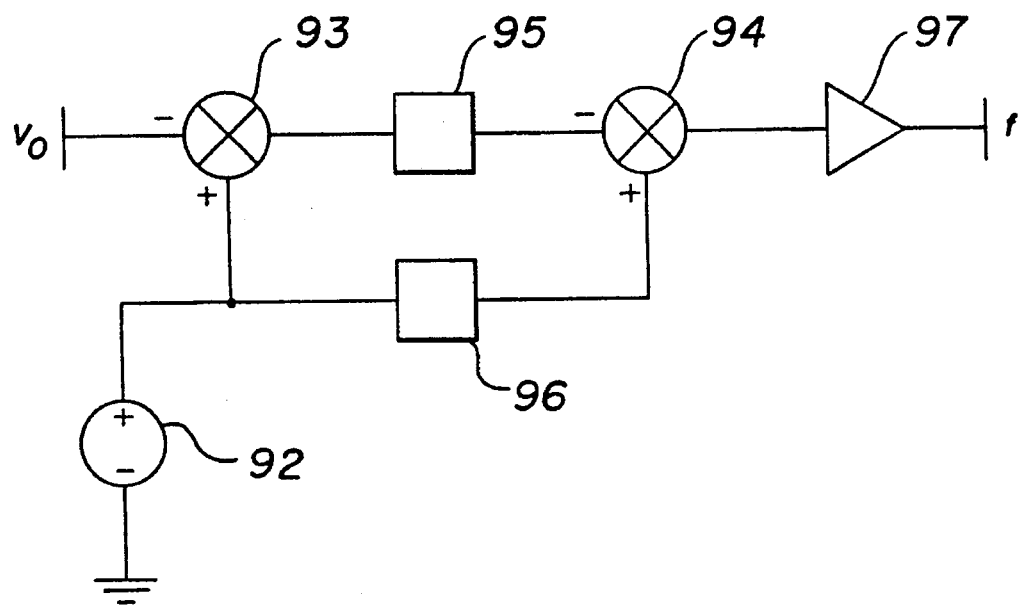
FIG. 9 depicts a processing means according to the present invention.

The procedure of Example 2 is repeated, except that the processing means is a circuit such as depicted in FIG. 9, having means for providing a voltage $G_s$ (92), means for signal addition (93 or 94), means for applying a logarithm function (95 or 96), and amplification means (97) having a gain of $\beta_{test}$.

EXAMPLE 4

An unknown test gas is passed at a fixed, yet unknown, flow rate through the system depicted in FIG. 3. It is desired to pass the test gas through the system at a flow rate of 500 sccm.

After a short interval, the passage of the fluid is terminated. The input voltage required to maintain the heating means 160° C. above the ambient temperature is recorded at 6.3 volts. The output signal is recorded as 1.0 volts. Passage of the fluid is then resumed.

The input voltage and the output signal are provided as a data set to a processing means. The input voltage is compared with the reference input voltages generated in Example 1 and the identity of the test gas is determined to be helium.

A flow function is then applied via the processing means to the data set according to:

$$f=\beta_{test}*[Log_e(G_s)-Log_e(G_s-\{v_o-V_{offset}\})] \quad (17)$$

where f is the fixed flow rate, $\beta_{test}$ is the constant determined in Example 1 for helium, $G_s$ is an experimentally derived constant voltage dependent upon the conduit, $v_o$ is the output signal, and $V_{offset}$ is the output signal at zero flow, 1.0 volts in the present case.

The flow function is solved for f, the flow rate, and found to be 400 sccm. Since this value is lower than 500 sccm, the fixed flow rate is increased. The flow rate is re-calculated and the fixed flow rate adjusted until the calculated flow rate is equal to 500 sccm.

EXAMPLE 5

An unknown test gas is passed through the system depicted in FIG. 3 at a fixed, yet unknown, flow rate. It is desired to pass the test gas through the system at a flow rate of 500 sccm.

The input voltage required to maintain the heating means 160° C. above the ambient temperature is recorded as 6.6 volts. The output signal is recorded as 0.2 volts. The input voltage and output signal are provided to a processing means as a data set.

The input voltage is compared with the reference input voltages generated in Example 1. The identity of the test gas cannot conclusively be determined by such a comparison, as its input voltage is between the reference input voltages for helium (6.3 volts) and hydrogen (6.9 volts). Therefore, the input voltage of the test gas at an output signal of 0.2 volts is compared with the input voltages for helium and hydrogen at an output signal of 0.2 volts, and the test gas is identified as helium. Air is selected as the reference fluid with which the test gas will be compared.

A flow function is then applied via the processing means to the data set according to:

$$f=\beta_{test}\{[(\rho C_p/k)_{ref}]/[(\rho C_p/k)_{test}]\}*[Log_e(G_s)-Log_e(G_s-v_o)] \quad (18)$$

where f is the fixed flow rate, $\beta_{test}$ is the constant determined in Example 1 for helium, $(\rho C_p/k)_{ref}$ relates to air, $(\rho C_p/k)_{test}$ relates to the test gas, $\rho$ is the density of the gas, $C_p$ is the thermal capacity of the gas, k is the thermal conductivity of the gas, $G_s$ an experimentally derived constant voltage dependent upon the conduit, and $v_o$ is the output signal.

The flow function is solved for f, the flow rate, and found to be 400 sccm. Since this value is lower than 500 sccm, the fixed flow rate is increased. The flow rate is re-calculated and the fixed flow rate adjusted until the calculated flow rate is equal to 500 sccm.

EXAMPLE 6

The procedure of Example 5 is repeated, except that a flow function is applied via the processing means to the data set according to:

$$f=+\beta_{test}*\{[(\rho C_p/k)_{ref}]/[(\rho C_p/k)_{test}]\}*[Log_e(\alpha_{test}G_s)-Log_e(\alpha_{test}G_s-v_o)] \quad (19)$$

where f is the fixed flow rate, $\alpha_{test}$ and $\beta_{test}$ are the constants determined in Example 1 for helium, $(\rho C_p/k)_{ref}$ relates to air, $(\rho C_p/k)_{test}$ relates to the test gas, $\rho$ is the density of the gas, $C_p$ is the thermal capacity of the gas, k is the thermal conductivity of the gas, $G_s$ is an experimentally derived constant voltage dependent upon the conduit, and $v_o$ is the output signal.

Those skilled in the art will appreciate that numerous changes and modification may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for determining the flow rate of a test fluid, comprising the steps of:

determining the identity of the test fluid;

passing the test fluid through a conduit that comprises a first sensor, a second sensor a first predetermined distance from the first sensor, and a heating means;

providing an input voltage to the heating means to maintain the heating means at a temperature greater than the temperature of the conduit;

generating an output signal indicative of the temperature difference between the first and second sensors;

providing to a processing means a data set which comprises said output signal;

applying, via the processing means, a flow function to the data set according to:

$$u=(\rho CpL/k)^{-1}*(Log_e(\Psi)-Log_e(\Psi-\Delta T))]$$

where $\rho$ is the density of the identified test fluid, $C_p$ is the thermal capacity of the identified test fluid, L is a predetermined distance, k is the thermal conductivity of the identified test fluid, $\Psi$ is constant which depends upon the geometry of the conduit, and $\Delta T$ is the temperature difference between the first sensor and the second sensor, to determine the flow rate, u, of the test fluid.

2. A method for determining the flow rate of a test fluid, comprising the steps of:

determining the identity of the reference fluid;

passing the test fluid through a conduit that comprises a first sensor, a second sensor a first predetermined distance from the first sensor, and a heating means;

providing an input voltage to the heating means to maintain the heating means at a temperature greater than the temperature of the conduit;

generating a test output signal indicative of the temperature difference between the first and second sensors; and determining the flow rate of the test fluid on the basis of a data set and a flow function, said data set including said test output signal and said flow function identifying the flow rate as a function of at least the test output signal;

wherein the flow function is applied to the data set according to:

$$f=\beta_{test}*(Log_e(G_s)-Log_e(G_s-v_o))$$

where $\beta_{test}$ is an experimentally derived constant dependent upon the conduit and the identified test fluid, $G_s$ is an experimentally derived constant voltage dependent upon the conduit, and $v_o$ is the output signal, to determine the flow rate, f, of the identified test fluid.

3. A method for determining the flow rate of a test fluid, comprising the steps of:

determining the identity of the test fluid;

passing the test fluid through a conduit that comprises a first sensor, a second sensor a first predetermined distance from the first sensor, and a heating means;

providing an input voltage to the heating means to maintain the heating means at a temperature greater than the temperature of the conduit;

generating a test output signal indicative of the temperature difference between the first and second sensors; and determining the flow rate of the test fluid on the basis of a data set and a flow function, said data set including said test output signal and said flow function identifying the flow rate as a function of at least the test output signal;

wherein the flow function is applied to the data set according to:

$$f=\beta_{test}*(Log_e(G_s)-Log_e(G_s-\{v_o-V_{offset}\}))$$

where $\beta_{test}$ is an experimentally derived constant dependent upon the conduit and the identified test fluid, $G_s$ is an experimentally derived constant voltage dependent upon the conduit, $v_o$ is the output signal, and $V_{offset}$ is the output signal at zero flow, to determine the flow rate, f, of the identified test fluid.

4. A method for determining the flow rate of a test fluid, comprising the steps of:

determining the identity of the test fluid;

passing the test fluid through a conduit that comprises a first sensor, a second sensor a first predetermined distance from the first sensor, and a heating means;

providing an input voltage to the heating means to maintain the heating means at a temperature greater than the temperature of the conduit;

generating a test output signal indicative of the temperature difference between the first and second sensors; and determining the flow rate of the test fluid on the basis of a data set and a flow function, said data set including said test output signal and said flow function identifying the flow rate as a function of at least the test output signal;

wherein the flow function is applied to the data set according to:

$$f=\beta_{test}\{((\rho C_p/k)_{ref})/((\rho C_p/k)_{test})\}*(Log_e(G_s)-Log_e(G_s-v_o))$$

where $\beta_{test}$ is an experimentally derived constant dependent upon the conduit and the identified test fluid, $(\rho C_p/k)_{ref}$ relates to a reference fluid, $(\rho C_p/k)_{test}$ relates to the identified test fluid, $\rho$ is the density of the fluid, $C_p$ is the thermal capacity of the fluid, k is the thermal conductivity of the fluid, $G_s$ an experimentally derived constant voltage dependent upon the conduit, and $v_o$ is the test output signal, to determine the flow rate, f, of the identified test fluid.

5. The method of claim 4 wherein the reference fluid is a gas.

6. The method of claim 4 wherein the reference fluid is air.

7. A method for determining the flow rate of a test fluid, comprising the steps of:

determining the identity of the test fluid;

passing the test fluid through a conduit that comprises a first sensor, a second sensor a first predetermined distance from the first sensor, and a heating means;

providing an input voltage to the heating means to maintain the heating means at a temperature greater than the temperature of the conduit;

generating a test output signal indicative of the temperature difference between the first and second sensors; and determining the flow rate of the test fluid on the basis of a data set and a flow function, said data set including said test output signal and said flow function identifying the flow rate as a function of at least the test output signal;

wherein the flow function is applied to the data set according to:

$$f=\beta_{test}\{((\rho C_p/k)_{ref})/((\rho C_p/k)_{test})\}*(Log_e(\alpha_{test}G_s)-Log_e(\alpha_{test}G_s-v_o))$$

where $\alpha_{test}$ and $\beta_{test}$ are experimentally derived constants dependent upon the conduit and the identified test fluid, $(\rho C_p/k)_{ref}$ relates to a reference fluid, $(\rho C_p/k)_{test}$ relates to the identified test fluid, $\rho$ is the density of the fluid, $C_p$ is the thermal capacity of the fluid, k is the thermal conductivity of the fluid, $G_s$ is an experimentally derived constant voltage dependent upon the conduit, and $v_o$ is the test output signal, to determine the flow rate, f, of the identified test fluid.

8. The method of claim 7 wherein the reference fluid is a gas.

9. The method of claim 7 wherein the reference fluid is air.

10. A method for determining the flow rate of a test fluid, comprising the steps of:

determining the identity of the test fluid;

passing the test fluid through a conduit that comprises a first sensor, a second sensor a first predetermined distance from the first sensor, and a heating means;

providing an input voltage to the heating means to maintain the heating means at a temperature greater than the temperature of the conduit;

generating a test output signal indicative of the temperature difference between the first and second sensors; and determining the flow rate of the test fluid on the basis of a data set and a flow function, said data set including said test output signal and said flow function identifying the flow rate as a function of at least the test output signal;

further comprising:
   passing at least one reference fluid through the conduit;
   maintaining the heating means at a temperature greater than the temperature of the conduit in the presence of said at least one reference fluid; and
   generating a reference output signal.

11. A method for providing linearized output signals, comprising the steps of:

passing a test fluid through a conduit at a plurality of flow rates;

providing a plurality of input voltages to a heating means associated with the conduit to maintain the heating means at a temperature greater than the temperature of the conduit as said test fluid is passed through said conduit at said plurality of flow rates;

generating a test output signal at each of the plurality of flow rates;

providing to a processing means a data set which comprises the test output signals; and applying, via the processing means, a linearizing function to the data set according to:

$$f=-\beta_{test}*(Log_e(\alpha_{test})-Log_e(\alpha_{test}-v_o))$$

where $\alpha_{test}$ and $\beta_{test}$ are experimentally derived constants dependent upon the conduit and the test fluid, and $v_o$ is the test output signal, to provide a linearized output signal, f.

12. A method for compiling reference constants, comprising the steps of:

passing a test fluid through a conduit at a known flow rate;

providing an input voltage to a heating means associated with the conduit to maintain the heating means at a temperature greater than the temperature of the conduit;

generating an output signal;

providing to a processing means a data set which comprises the output signal;

applying, via the processing means, a flow function to the data set according to:

$$f=-\beta_{test}*(Log_e(\alpha_{test})-Log_e(\alpha_{test}-v_o))$$

where f is the known flow rate and $v_o$ is the output signal, to determine reference constants, $\alpha_{test}$ and $\beta_{test}$, dependent upon the conduit and the reference fluid; and recording the reference constants.

13. A system for determining the flow rate of a fluid, comprising:

a conduit which comprises:
a first sensor;
a second sensor a predetermined distance from the first sensor; and
a heating means between the first sensor and the second sensor;

an output means, coupled with the first sensor and the second sensor, for generating an output signal representative of the difference in temperature between the first sensor and the second sensor;

a voltage source, coupled with the heating means, for providing input voltage thereto;

a means for passing the fluid through the conduit; and a processing means for applying a flow function to a data set which comprises the output signal, to determine the flow rate of the fluid, said flow function being in accordance with one of the following group:

$$u=(\rho C_p L/k)^{-1}*(Log_e(\Psi)-Log_e(\Psi-\Delta T)) \quad (a)$$

where $\rho$ is the density of the identified test fluid, $C_p$ is the thermal capacity of the identified test fluid, L is a predetermined distance, k is the thermal conductivity of the identified test fluid, $\Psi$ depends at least upon the geometry of the conduit, $\Delta T$ is the temperature difference between the first sensor and the second sensor, and u represents the flow rate of the test fluid;

$$f=\beta_{test}*(Log_e(G_s)-Log_e(G_s-v_o)) \quad (b)$$

where $\beta_{test}$ is an experimentally derived constant dependent upon the conduit and the identified test fluid, $G_s$ is an experimentally derived constant voltage dependent upon at least the conduit, $v_o$ is the output signal, and f represents the flow rate of the identified test fluid;

$$f=\beta_{test}*(Log_e(G_s)-Log_e(G_s-\{v_o-V_{offset}\})) \quad (c)$$

where $V_{offset}$ is the output signal at zero flow;

$$f=\beta_{test}\{((\rho C_p/k)_{ref})/((\rho C_p/k)_{test})\}*(Log_e(G_s)-Log_e(G_s-v_o)), \quad (d)$$

where $(\rho C_p/k)_{ref}$ relates to a reference fluid, $(\rho C_p/k)_{test}$ relates to the identified test fluid, $\rho$ is the density of the fluid, $C_p$ is the thermal capacity of the fluid, and k is the thermal conductivity of the fluid; and $$f=\beta_{test}*\{((\rho C_p/k)_{ref})/((\rho C_p/k)_{test})\}*(Log_e(\alpha_{test}G_s)-Log_e(\alpha_{test}G_s-v_o)), \quad (e)$$

where $\alpha_{test}$ is an experimentally derived constant dependent upon the conduit and the identified test fluid.

14. A system for providing linearized output signals, comprising:

a conduit which comprises:
a first sensor;
a second sensor a predetermined distance from the first sensor; and
a heating means between the first sensor and the second sensor;

an output means, coupled with the first sensor and the second sensor, for generating an output signal representative of the difference in temperature between the first sensor and the second sensor;

a voltage source, coupled with the heating means, for providing input voltage thereto;

a means for determining the flow rate of the fluid;

a means for passing the fluid through the conduit; and a processing means for applying a linearizing function to a data set comprising the output signal according to:

$$f=-\beta_{test}*(Log_e(\alpha_{test})-Log_e(\alpha_{test}-v_o))$$

where $\alpha_{test}$ and $\beta_{test}$ are experimentally derived constants dependent upon the conduit and the test fluid, and $v_o$ is the test output signal, to provide a linearized output signal, f.

15. A method for determining the identity and flow rate of a test fluid, comprising the steps of:

(a) passing a test fluid through a conduit comprising first and second sensors and a heater;

(b) maintaining said heater at a temperature greater than the temperature of the conduit by applying a heater voltage to said heater;

(c) generating a first data value on the basis of said heater voltage and comparing said first data value with a first reference to determine the identity of said test fluid;

(d) generating a test output signal indicative of a difference in temperature between said first and second sensors;

(e) generating a second data value indicative of the test fluid flow rate, said second data value being a function of the test fluid identity and the test output signal;

wherein step (e) comprises applying a flow function to the second data value to determine the flow rate of the test fluid;

wherein the flow function is selected from the following group:

$$u=(\rho C_p L/k)^{-1}*(Log_e(\Psi)-Log_e(\Psi-\Delta T)) \quad (1)$$

where ρ is the density of the identified test fluid, $C_p$ is the thermal capacity of the identified test fluid, L is a predetermined distance, k is the thermal conductivity of the identified test fluid, Ψ depends at least upon the temperature of the heater, ΔT is the temperature difference between the first sensor and the second sensor, and u represents the flow rate of the test fluid;

$$f=\beta_{test}*(Log_e(G_s)-Log_e(G_s-v_o)) \quad (2)$$

where $\beta_{test}$ is an experimentally derived constant dependent upon the conduit and the identified test fluid, $G_s$ is a voltage dependent at least upon the temperature of the heating means, $v_o$ is the output signal, and f represents the flow rate of the identified test fluid;

$$f=\beta_{test}*(Log_e(G_s)-Log_e(G_s-\{v_o-V_{offset}\})) \quad (3)$$

where $V_{offset}$ is the output signal at zero flow;

$$f=\beta_{test}\{((\rho C_p/k)_{ref})/((\rho C_p/k)_{test})\}*(Log_e(G_s)-Log_e(G_s-v_o)), \quad (4)$$

where $(\rho C_p/k)_{ref}$ relates to a reference fluid, $(\rho C_p/k)_{test}$ relates to the identified test fluid, ρ is the density of the fluid, $C_p$ is the thermal capacity of the fluid, and k is the thermal conductivity of the fluid; and $$f=\beta_{test}*\{((\rho C_p/k)_{ref})/((\rho C_p/k)_{test})\}*(Log_e(\alpha_{test}G_s)-Log_e(\alpha_{test}G_s-v_o)), \quad (5)$$

where $\alpha_{test}$ is an experimentally derived constant dependent upon the conduit and the identified test fluid.

16. Apparatus for determining the identity and flow rate of a test fluid, comprising:

(a) means for passing a test fluid through a conduit comprising first and second sensors and a heater;

(b) means for maintaining said heater at a temperature greater than the temperature of the conduit by applying a heater voltage to said heater;

(c) means for generating a first data value on the basis of said heater voltage and comparing said first data value with a first reference to determine the identity of said test fluid;

(d) means for generating a test output signal indicative of a difference in temperature between said first and second sensors; and (e) means for generating a second data value indicative of the test fluid flow rate, said second data value being a function of the test fluid identity and the test output signal;

wherein said means for generating a second data value comprises means for applying a flow function to the second data value to determine the flow rate of the test fluid;

wherein said means for applying a flow function to the second data value comprises means for applying a flow function selected from the following group:

$$u=(\rho CpL/k)^{-1}*(Log_e(\Psi)-Log_e(\Psi-\Delta T)) \quad (1)$$

where ρ is the density of the identified test fluid, $C_p$ is the thermal capacity of the identified test fluid, L is a predetermined distance, k is the thermal conductivity of the identified test fluid, Ψ is constant which depends at least upon the temperature of the heater, ΔT is the temperature difference between the first sensor and the second sensor, and u represents the flow rate of the test fluid;

$$f=\beta_{test}*(Log_e(G_s)-Log_e(G_s-v_o)) \quad (2)$$

where $\beta_{test}$ is an experimentally derived constant dependent upon the conduit and the identified test fluid, $G_s$ is a voltage dependent upon the temperature of the heater, $v_o$ is the output signal, and f represents the flow rate of the identified test fluid;

$$f=\beta_{test}*(Log_e(G_s)-Log_e(G_s-\{v_o-V_{offset}\})) \quad (3)$$

where $V_{offset}$ is the output signal at zero flow;

$$f=\beta_{test}\{((\rho C_p/k)_{ref})/((\rho C_p/k)_{test})\}*(Log_e(G_s)-Log_e(G_s-v_o)), \quad (4)$$

where $(\rho C_p/k)_{ref}$ relates to a reference fluid, $(\rho C_p/k)_{test}$ relates to the identified test fluid, ρ is the density of the fluid, $C_p$ is the thermal capacity of the fluid, and k is the thermal conductivity of the fluid; and $$f=\beta_{test}*\{((\rho C_p/k)_{ref})/((\rho C_p/k)_{test})\}*(Log_e(\alpha_{test}G_s)-Log_e(\alpha_{test}G_s-v_o)), \quad (5)$$

where $\alpha_{test}$ is dependent upon the temperature of the heater.

* * * * *